United States Patent [19]

Crownover

[11] Patent Number: 4,635,735

[45] Date of Patent: Jan. 13, 1987

[54] METHOD AND APPARATUS FOR THE CONTINUOUS ANALYSIS OF DRILLING MUD

[75] Inventor: Donald J. Crownover, Houston, Tex.

[73] Assignee: Schlumberger Technology Corporation, New York, N.Y.

[21] Appl. No.: 628,683

[22] Filed: Jul. 6, 1984

[51] Int. Cl.[4] .................. E21B 47/00; C09K 7/00
[52] U.S. Cl. ...................... 175/48; 175/42; 175/50; 73/155
[58] Field of Search .............. 175/38, 42, 48, 50; 73/153, 155

[56] References Cited

U.S. PATENT DOCUMENTS

| | | | |
|---|---|---|---|
| 2,341,169 | 2/1944 | Wilson et al. | 73/153 X |
| 2,715,450 | 8/1955 | Bliss et al. | 73/153 X |
| 2,923,151 | 2/1960 | Engle et al. | 73/153 |
| 3,462,761 | 8/1969 | Horeth et al. | 73/153 X |
| 3,731,530 | 5/1973 | Tanguy et al. | 73/153 |
| 3,982,432 | 9/1976 | Hammond | 73/155 X |
| 4,492,862 | 1/1985 | Grynberg et al. | 250/255 |

*Primary Examiner*—Stuart S. Levy
*Assistant Examiner*—David Werner

[57] ABSTRACT

An oil well drilling rig (10) recirculates drilling mud which is analyzed continuously by pumping it through a gas separation unit (72) where the gases in the mud become separated and mixed with a carrier gas and are conveyed to gas analyzing devices (196) where the concentration of the different hydrocarbon components of the gases in the mud are continuously measured and the signals representative of these measurements are processed together with mud flow rate, and the carrier gas flow rate or the sample gas flow rate signals in a signal processor (64) to provide a continuous log of gas component concentration during drilling.

56 Claims, 6 Drawing Figures

METHOD AND APPARATUS FOR THE CONTINUOUS ANALYSIS OF DRILLING MUD

BACKGROUND OF THE INVENTION

1. Field of the Invention

This invention relates to well logging during drilling and in particular it concerns a novel method and apparatus for continuously analyzing the gases returned in the drilling mud from a well as it is being drilled.

2. Description of the Prior Art

In the drilling of an oil or gas well, a drill bit is mounted on the end of an elongated rotating drill string which turns the bit and causes it to cut away the underlying earth and rock formations. During this operation a drilling mud is continuously pumped down through the drill string and into the region around the drill bit and then back up to the surface. This drilling mud is typically made up of clays, chemical additives and an oil or water base and performs two important functions. First, it serves to cool and lubricate the drill bit and to carry drill cuttings back up out from the well. Secondly, the weight of the mud, which can be adjusted by controlling the amount of special weighting additives, serves to maintain a hydrostatic pressure to prevent pressurized fluids in the earth from blowing out through the drilled well.

During the drilling of a well, various measurements are taken from the drilling mud that is returned to the surface; and these measurements, which may optionally be taken together with other measurements made near the drill bit by MWD (measurements-while-drilling) tools, provide a log of the drilling operation which permits one to analyze the earth formations through which the drill bit is penetrating. This log is important because it enables the drilling operator to ascertain the presence of oil or gas in the formation being drilled.

In the past, continuous mud logging measurements have been made during drilling. These continuous measurements included the temperature, electrical conductivity, pH, sulfide ion content and oxidation-reduction potential of the drilling mud returned from the well. In addition, continuous measurements have been made on the returning mud to ascertain its total hydrocarbon content and to ascertain the presence of certain specific gases such as carbon dioxide and hydrogen sulfide in the mud.

Past well mud logging techniques have also made use of gas chromatography to ascertain the presence of different hydrocarbon species in the mud being returned. As explained in a publication entitled "Formation Evaluation by Analysis of Hydrocarbon Ratios" by B. 0. Pixler and puolished in *Journal of Petroleum Technology*, June 1969 pp. 665-670, it is possible by comparing the ratios of methane to each of several other hydrocarbon gases, such as ethane, propane, butane and pentane, to estimate whether a well will be productive and, if so, whether the well will produce oil, gas or water.

The gas chromatography technique involves taking samples of gas from the drilling mud and passing that gas through special columns filled with materials that allow different gases to flow at different rates. The different gases are identified according to the length of time required for them to pass through the column. Because identification of the different gas species requires a comparison of passage time through the chromatograph columns, the measurements of the gas species are not made continuously but instead they must be taken at discrete intervals from two to four minutes apart. As a result it has not previously been possible to ascertain hydrocarbon species ratios on a continuous basis during a drilling operation; and therefore a complete analysis of the formations along the well has not been obtainable during a drilling operation. Also, the prior art technique did not permit one to ascertain changes in the relative concentrations of different hydrocarbon species at the earliest possible time during the drilling operation. As a result, the drilling operator could not be certain that he had not drilled through a productive stratum or that he was approaching a high pressure fluid region that might produce a dangerous "kick" or even a blowout of the well.

A further disadvantage of the prior art chromatographic gas analysis technique results from the fact that it is not possible to separate all of the hydrocarbon gas from the returning mud and therefore it is not possible with chromatographic analysis to ascertain the actual concentration of any species in the mud.

The prior art also fails to provide in an integrated, self-contained system, the adaptability to switch quickly between various types of tests and the various purges, zero settings and calibration of test elements and backwash of gas separation devices that are required for continuous gas analysis during the drilling of oil and gas producing wells.

SUMMARY OF THE INVENTION

The present invention overcomes the above described problems of the prior art.

In one aspect, the present invention provides a novel method and apparatus for producing a mud logging signal during a well drilling operation which represents, on a continuous basis, the instantaneous concentration ratio of different gaseous components in drilling mud as it is being returned from a well. According to this aspect, at least one portion of the drilling mud being returned from the well is subjected to gas separation in mud gas separation means, whereby the gas which includes various gaseous components to be analyzed is separated from the mud. Simultaneously with the separation of gas from the mud, the separated gas is continuously subjected to different analyses in gas analyzing means to produce different gaseous component concentration signals whose values at any instant represent, respectively, the concentrations at that instant of the different gaseous components in the separated gas. These different gaseous component concentration signals are processed continuously in signal processing means to provide a continuous logging signal whose value at any instant represents the ratio of the values of the gaseous component concentration signals and thus provides an indication of the instantaneous concentration ratio of the different gaseous components in the drilling mud.

In another aspect, the present invention makes possible the provision of a logging signal which represents, on a continuous basis, the instantaneous concentration of a given gaseous component of drilling mud as it is returned from a well being drilled. According to this second aspect at least a portion of the drilling mud being returned from the well is subjected to gas separation in mud gas separation means, whereby the gas which includes various gaseous components to be analyzed is separated from the mud. Simultaneously with the separation of gas from the mud, the separated gas is continuously subjected to analysis in gas analyzing means to produce a gaseous component concentration signal whose value at any instant represents the concentration, at that instant, of the given gaseous component in the separated gas. The flow rate of the returned mud portion and the flow rate of the separated gas are measured continuously in mud and gas flow rate measuring means to produce a continuous mud flow rate signal and a continuous gas flow rate signal whose values correspond, respectively, to the instantaneous rates of flow of the drilling mud from which the gas is separated and of the separated gas itself. The gaseous component concentration signal, the mud flow rate signal and the gas flow rate signal are processed continuously in signal processing means to produce a continuous logging signal whose value at any instant corresponds to the product of the concentration at that instant of the given gaseous component and the rate of flow at that instant of the separated gas divided by the rate of flow at that instant of the drilling mud. This provides a continuous representation of the concentration of the given gaseous component in the drilling mud.

In a third aspect of the present invention, the concentration of a given component of the mud gas in a drilling mud is ascertained even though it is not possible to completely separate the gas from the mud. According to this third aspect, the drilling mud is passed through an agitating type mud gas separation device while a carrier gas is simultaneously flowed through the mud gas separation device at a rate such that the volume of carrier gas is at least several times greater than the volume of mud gas in the drilling mud. The carrier gas is thoroughly mixed in the mud gas separation device with all of the mud therein as well as with the mud gas contained in the mud. The resulting mixture of carrier gas and mud gas is separated from the mud gas separation device and is subjected to analysis in gas analyzing means to produce a component gas signal whose value corresponds to the concentration of the component in the gas mixture. The volume of the carrier gas flowing into the mud gas separation device is measured continuously in gas rate measuring means to produce a carrier gas flow rate signal. The flow rate of the mud which passes through the mud gas separation device is also measured in mud flow rate measuring means to produce a mud flow rate signal. The component gas signal, the carrier gas flow rate signal and the mud flow rate signal are combined continuously in a signal processing means such that the product of the values of the component gas and carrier gas flow rate signals is divided by the value of the mud flow rate signal. This provides a concentration signal whose value represents the concentration of the component gas in the drilling mud.

In a still further aspect, the present invention provides an integrated system for enabling continuous testing of drilling mud gas as well as convenient switching to zero setting, backwash of the gas separation devices, and purge and calibration of the testing devices. According to this aspect there is provided a mud gas test system for testing the gases contained in drilling mud returned from a well being drilled. The system comprises a gas analyzing device for analyzing gases separated from the drilling mud, a mud gas separation device having a mud inlet and a mud outlet and a carrier gas inlet and a gas mixture outlet. The mud gas separation device is of the type in which carrier gas is mixed with mud passing through it to produce a gas mixture with gas contained in the mud. First and second manifolds are connected, respectively, to the carrier gas inlet and the gas mixture outlet. Means are arranged to supply a carrier gas to the first manifold and means, including a first valve, connects the carrier gas inlet of the mud gas separation device to the first manifold. Means including a second valve connects the gas mixture outlet of the mud gas separation device to the second manifold and means including a third valve interconnects the first and second manifolds. Further means interconnects the second manifold to the gas analyzing device.

The above described manifold and valve arrangement permits convenient and rapid switching between zero setting of and testing by the gas analyzing device. Furthermore by providing appropriate additional valves, calibration gas sources and other gas separation devices, it is possible to provide purging and calibration of the gas analyzing device as well as backwashing of the gas separation device so that different tests can be performed in rapid sequence.

BRIEF DESCRIPTION OF THE DRAWINGS

A preferred embodiment of the invention has been chosen for purposes of description and illustration and is shown herein in the accompanying drawings forming part of this specification, wherein.

DETAILED DESCRIPTION OF THE PREFERRED EMBODIMENT

Figure 1:
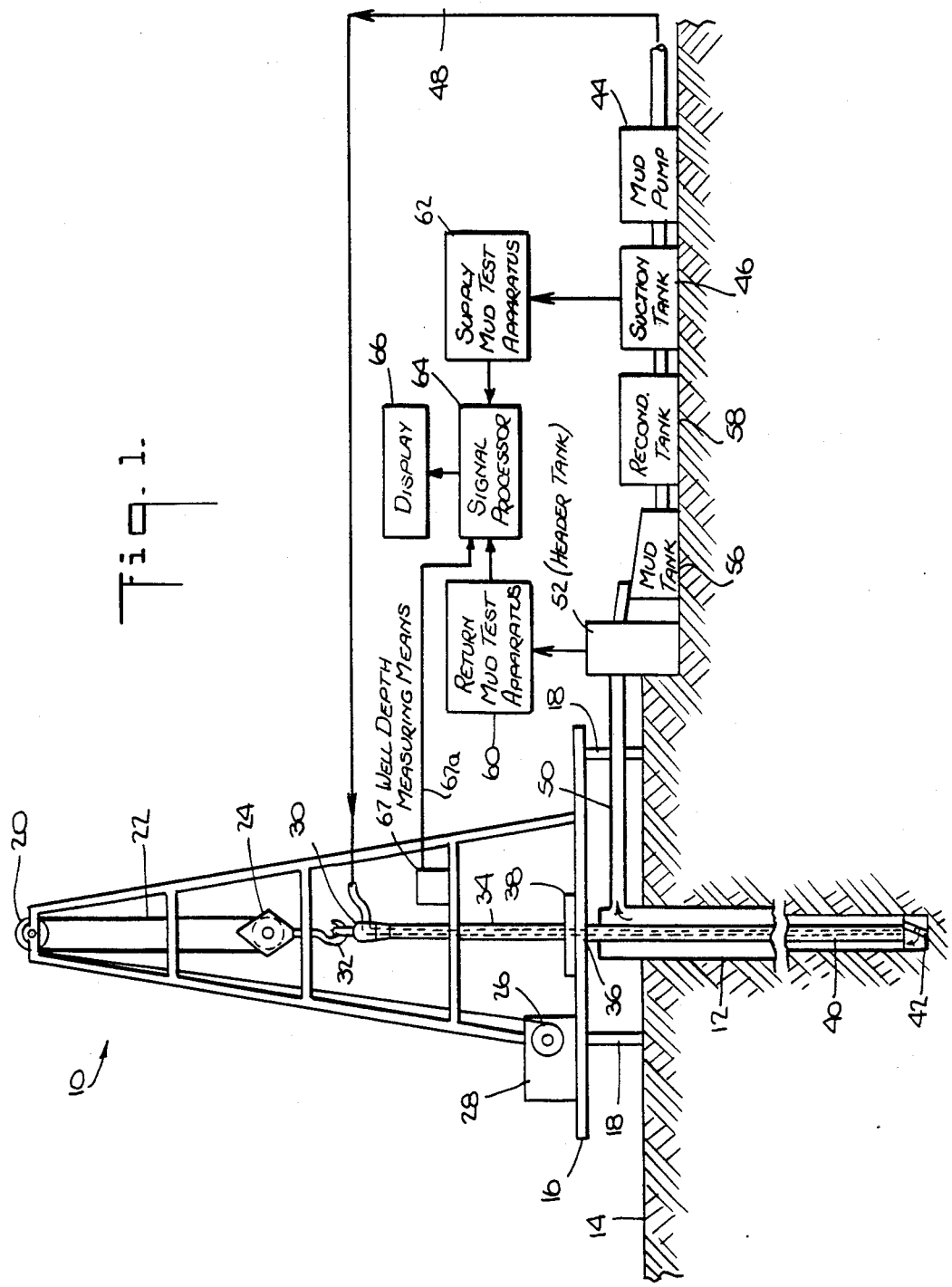
FIG. 1 is a diagrammatic representation of well drilling and associated mud processing equipment in which the present invention is embodied.

FIG. 1 shows schematically a drilling tower 10 mounted over a wall 12 being drilled in the earth 14. The drilling tower 10 is mounted on a platform 16 which is supported over the well 12 on legs 18 or other suitable structures. A fixed block 20 is mounted at the top of the tower 10 and is connected via several loops of a hoisting cable 22 to a traveling block 24. The hoisting cable 22 extends down from the fixed block to a drawworks drum 26 on the platform 16. The drawworks drum is rotated by a suitable drawworks motor, clutch and brake arrangement indicated schematically at 28.

A swivel connector 30 is suspended, by means of a hook and eye 32, from the traveling block 24. The lower part of the swivel connector 30 is attached to the upper end of an elongated kelly 34 which extends down through an opening 36 in the platform 16 above the well 12. The kelly 34 also passes through a turntable 38 mounted on the platform 16 over the opening 36. The kelly 34 has a noncircular cross section which fits loosely but closely in a correspondingly shaped opening in the turntable 38. Thus, as the turntable 38 rotates it causes the kelly 34 to turn; but the kelly remains free to move up and down through the turntable. A suitable drive means (not shown) is mounted on the platform 16 to rotate the turntable 38.

A drill string 40, made up of a series of elongated drill pipes connected end-to-end, is suspended from the bottom of the kelly 34. This drill string extends down through the well 12 to the bottom thereof. A drill bit 42 is mounted on the bottom of the drill string.

During a drilling operation the turntable 38 is rotated to turn the kelly 34 and the drill string 40, thereby causing the drill bit 42 to turn in the earth 14 at the bottom of the well 12. The drill bit cuts into the earth and any rock or other formations encountered. The rotation of the drill bit, drill string and kelly is isolated from the traveling block 24 by the swivel connection 30. As the drill bit 42 turns, the drawworks motor, clutch and brake mechanism 28 is operated to turn the drawworks drum 26 which feeds the hoisting cable 22 to the fixed block 20 to lower the travelling block 24. This allows the drill string 40 and drill bit 42 to be lowered further into the earth as drilling proceeds.

During the drilling operation, a drilling mud is pumped by means of a mud pump 44 from a suction tank 46 through a mud supply line 48 to the swivel connector 30. The swivel connector 30, the kelly 34 and the drill string 40 are hollow and the mud is pumped through them down to the drill bit 42 at the bottom of the well. The mud then proceeds back up through the annular space between the drill string 40 and the sides of the well 12 to the top of the well where it is directed via a mud return line 50 to a header tank 52. The mud passes from the header tank 52 to a shale shaker 54 and then into a mud tank 56. The shale shaker 54 separates pieces of rock and other cuttings acquired by the mud from around the region of the drill bit. The mud then passes from the mud tank 56 to a reconditioning tank 58 where mud additives are provided. The reconditioned mud is then transferred to the suction tank 46 for recycling through the system.

The drilling and mud recirculation equipment thus far described are well known and their particular details do not per se form part of this invention. Accordingly, this equipment will not be described in further detail.

The mud which circulates down to the bottom of the well 12 and back provides several functions. First, it cools and lubricates the drill bit 42. Second, it carries cuttings produced by the drill bit back out of the well being drilled. Third, it provides a support for the wellbore wall. Fourth (and of special importance), the mud in the well 12 provides hydrostatic pressure to counter the pressure of earth formation fluids encountered during drilling. This hydrostatic pressure prevents blowouts which are extremely dangerous and costly.

The mud may also be used to provide power to drive a drill bit motor attached to the drill bit at the bottom of the well and it may also be used as an acoustic transmission medium through which pressure impulses generated in response to sensing transducers at the bottom of the well are transmitted to the surface.

A further function provided by the mud recirculating in the well is that it provides, by virtue of its changed chemistry, an indication of the conditions at the bottom of the well and thereby permits logging of the well during drilling. The present invention is directed particularly to this further function. As shown in FIG. 1 there is provided a return mud testing apparatus 60 which is connected to take a sample of mud from the header tank 52, test the sample and return it to the header tank. Likewise there is provided a supply mud testing apparatus 62 which is connected to take a sample of mud from the suction tank 46, test the sample and return it to the suction tank. Test signals from these apparatus are supplied to a signal processor 64 which produces an output at a display 66.

There is also provided a well depth measuring means 67 mounted on the tower 10. This measuring means monitors the downward movement of the kelly 34 and produces corresponding signals on a well depth signal line 67a which directs the signals to the signal processor 64. As each new length of drill pipe is added to the drill string 40 and the kelly is raised, the additional length is entered into the measuring means 67 so that its output signals always represent the actual depth of the well. These signals are correlated with the various measurement signals in the signal processor 64 to provide a continuous log of measured characteristics correlated with the depth of the well.

Figure 2:
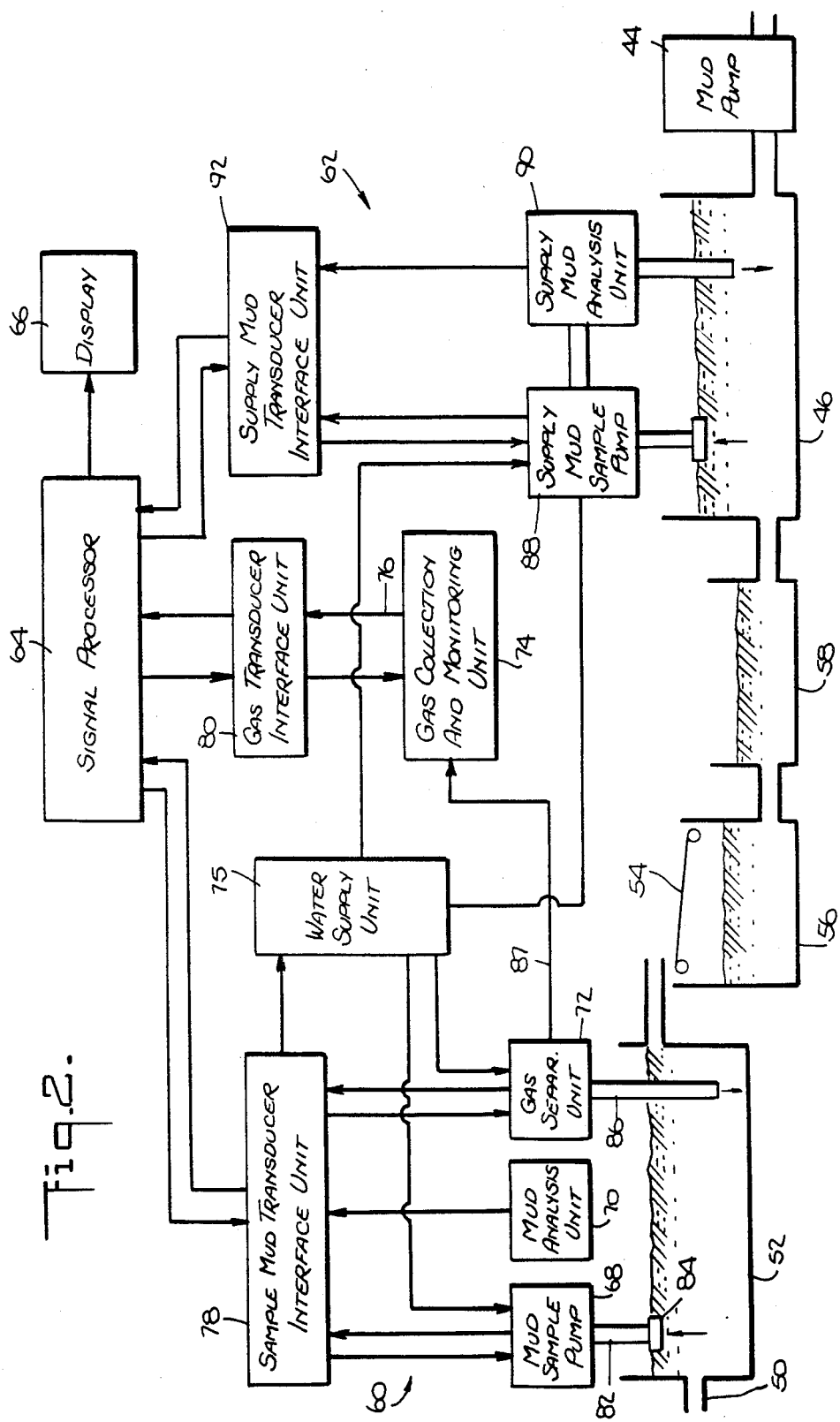
FIG. 2 is a block diagram showing the major components of a mud analysis system used in conjunction with the mud processing equipment of FIG. 1.

The components of the return mud testing apparatus 60 and the supply mud testing apparatus 62 are shown in FIG. 2. As can be seen in FIG. 2, the return mud testing apparatus 60 includes a mud sample pump 68, a mud analysis unit 70, a gas separation unit 72 and a gas collection and monitoring unit 74. In addition, there are provided a water supply unit 75 and sample mud and gas transducer interface units 78 and 80. Electrical signals representative of measurements taken in the gas collection and monitoring unit 74 are transmitted via gas analysis signal lines 76 to the gas transducer interface unit 80.

The mud sample pump 68 is provided with an inlet line 82 connected to a float 84 which floats on top of the mud in the header tank 52 near the inlet from the mud return line 50. This arrangement ensures that the mud sample to be analyzed will be taken from the mud just entering the header tank 52 from the well 12. Since the rate of mud flow through the well and the depth of the well are known, it is possible to relate the mud sample analysis to the location in the earth to which it pertains. The outlet of the mud sample pump 68 is connected to the mud analysis unit 70 where various chemical and electrical tests are performed on the mud sample. The mud sample then passes through the gas separation unit 72 where gases contained in the mud sample are extracted. The mud is then directed through a return line 86 back to the header tank 52. The gases extracted from the sample mud are directed via a sample gas line 87 to the gas collection and monitoring unit 74 where they are analyzed to ascertain their constituent parts and where other measurements are made. Signals which control the operation of the mud sample pump 68 and the gas separation unit 72 are supplied from the signal processor 64 via the mud transducer interface unit 78. Also, mud analysis signals from the mud analysis unit 70 are supplied via the mud transducer interface unit 78 to the signal processor 64. Gas analysis signals from the gas collection and monitoring unit 74 are supplied via the gas transducer interface unit 80 to the signal processor 64. The water supply unit 75 periodically supplies water to the mud sample pump 68, the mud analysis unit 70 and the gas separation unit 72 for cleaning purposes and its operation is controlled by signals supplied from the signal processor 64 via the mud transducer interface unit 78.

The supply mud testing apparatus 62 is similar in construction and operation to the return mud testing apparatus 60 except that no gas separation and monitoring is performed on the supply mud. Thus the supply mud testing apparatus 62 comprises only a supply mud sample pump 88 and a supply mud analysis unit 90. Controls for the pump 88 and signals from the analysis unit 90 are transmitted via a transducer interface unit 92 from and to, respectively, the signal processor 64. The water supply unit 75 is also connected to supply water periodically to the pump 88 and the analysis unit 90 for cleaning same.

Figure 3:
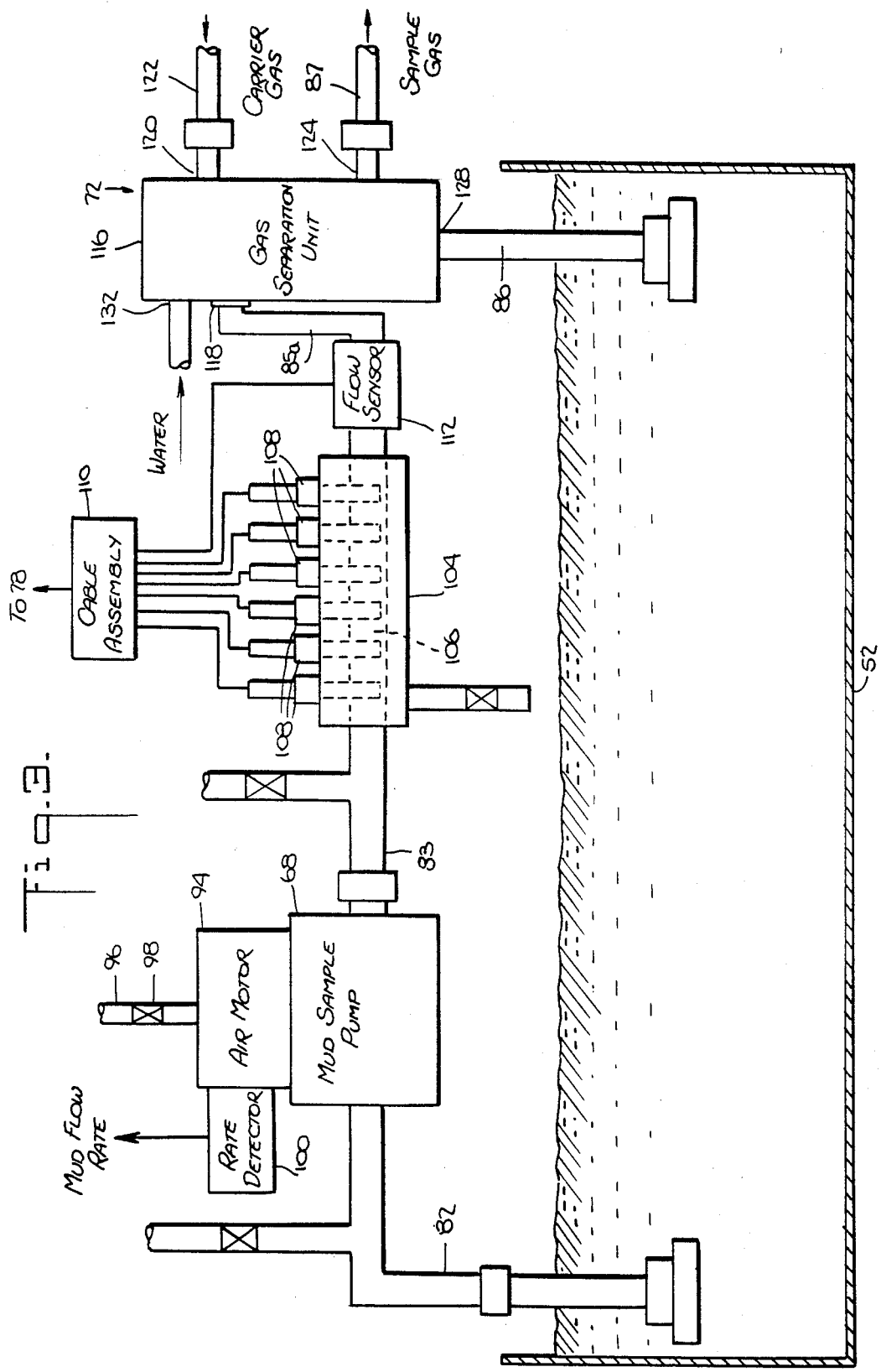
FIG. 3 is a diagrammatic representation of the components used to extract, pump and return mud to the mud processing equipment of FIG. 1 as well as to separate and analyze gas from the extracted mud.

The mud sample pump 68, the mud analysis unit 70 and the gas separation unit 72 are shown in greater detail in FIG. 3. The mud sample pump 68 is a positive displacement pump, for example, a progressive cavity pump or a peristaltic pump, capable of delivering a volume flow rate which is precisely proportional to the rate at which the pump is driven. As shown, the mud sample is taken from near the surface of the mud in the header tank 52 and this mud is supplied via the inlet line 82 to the pump and is driven by the pump through a connecting line 83 to the mud analysis unit 70. The pump 68 is driven by an air motor 94 which is supplied with pressurized air via an air supply line 96 from a suitable source (not shown). A control valve 98 is interposed in the supply line 96 to control the operation of the motor 94. A rate detector 100 is connected to the air motor 94. This rate detector produces a signal on a mud flow rate signal line 102 which is proportional to the motor and pump speeds and which therefore represents the mud flow rate through the pump. This signal is supplied via the mud transducer interface unit 78 (FIG. 2) to the signal processor 64 for processing in a manner to be described. The rate detector 100 is preferably a digital type and may constitute a magnetic pickup on the pump housing arranged to produce pulses when magnetic elements on the pump drive shaft pass under the pickup.

The mud sample pump 68 is driven at a measured rate such that the amount of mud pumped through it can be related to the total mud flow from the well.

The mud analysis unit 70 comprises a housing 104 formed with a passageway 106 through which mud from the mud sample pump 68 flows. A plurality of sensors 108 are mounted in the housing 104 and extend into the passageway 106. These sensors, which per se are known to those skilled in the art, serve to sense various characteristics of the mud flowing past them, such as acidity or pH, sulfide ion concentration, electrical conductivity, temperature and reduction-oxidation potential. The sensor outputs are supplied in the form of electrical signals to a cable assembly 110 which in turn is connected to the mud transducer interface unit 78 (FIG. 2) for transfer of the signals to the signal processor 64. The sample mud from the mud analysis unit 70 is directed via a further connecting line 85 to the gas separation unit 72.

A flow sensor 112 is interposed in the connecting line 85. This flow sensor, which may be of any suitable type, such as a pressure sensor, a pressure differential sensor, a vane or leaf sensor or a positive displacement flow sensor, produces an output signal when the mud flow rate through the mud analysis unit 70 falls below a predetermined threshold. This output signal is also supplied via the cable assembly 110 to the mud transducer interface unit 78 and the signal processor 64.

As shown in FIG. 3, the connecting line 85 has a vertical leg 85a between the flow sensor 112 and the gas separation unit 72. This vertical leg provides a hydrostatic head which maintains back pressure on the mud flowing through the mud analysis unit 70 so that if the pump 68 should stop pumping, the passageway 106 in the mud analysis unit 70 will always be filled with mud and the sensors 108 will always be fully immersed in the mud. It will be appreciated that if the mud analysis unit 70 is arranged with its passageway 106 extending vertically, the passageway itself cound serve to generate the hydrostatic head and in such case the vertical leg 85 in the connecting line 85 may be eliminated.

The gas separation unit 72 operates to extract gases from the sample mud which passes through the unit and to direct those gases out through a sample gas flow line 87 to the gas collection and monitoring unit 74 (FIG. 2). The gas separation unit 72 is preferably an aeration type, such as that shown and described in commonly-assigned U.S. patent application Ser. No. 501,038 filed June 6, 1983 in the name of Donald J. Crownover. The details of the gas separation unit are not part of this invention and will not be described here. In general, however, the aeration type separation device includes a housing 116 having a mud inlet 118 connected to receive mud from the connecting line 85, a carrier gas inlet 120 connected to receive carrier gas, such as air or nitrogen, supplied via a carrier gas line 122, a sample outlet 124 connected to supply a mixture of carrier gas and gas extracted from the mud to the sample gas line 87 and a mud outlet 128 connected to the mud return line 86 which directs mud from the gas separation unit back to the header tank 52. The housing 116 is also provided with a water inlet 132 through which water may be supplied from time to time for cleaning or flushing the interior of the housing.

The gas separation unit is provided with an internal impeller (not shown) which churns the mud flowing through the housing and causes the mud to aerate and mix intimately with the carrier gas supplied via the inlet 120. During the mixing of the mud and carrier gas the gas contained in the mud (i.e. the mud gas) becomes evenly mixed with the carrier gas, and the resulting mixture of mud gas and carrier gas (referred to herein as "sample gas") exits via the sample gas outlet 124 along with the carrier gas. The mixture of mud gas and carrier gas exits from the gas separation unit 72 through the sample gas outlet 124. The sample gas flows from the outlet 124 through the sample gas line 87 to the gas collection and monitoring unit 74 (FIG. 2) for analysis.

Figure 4:
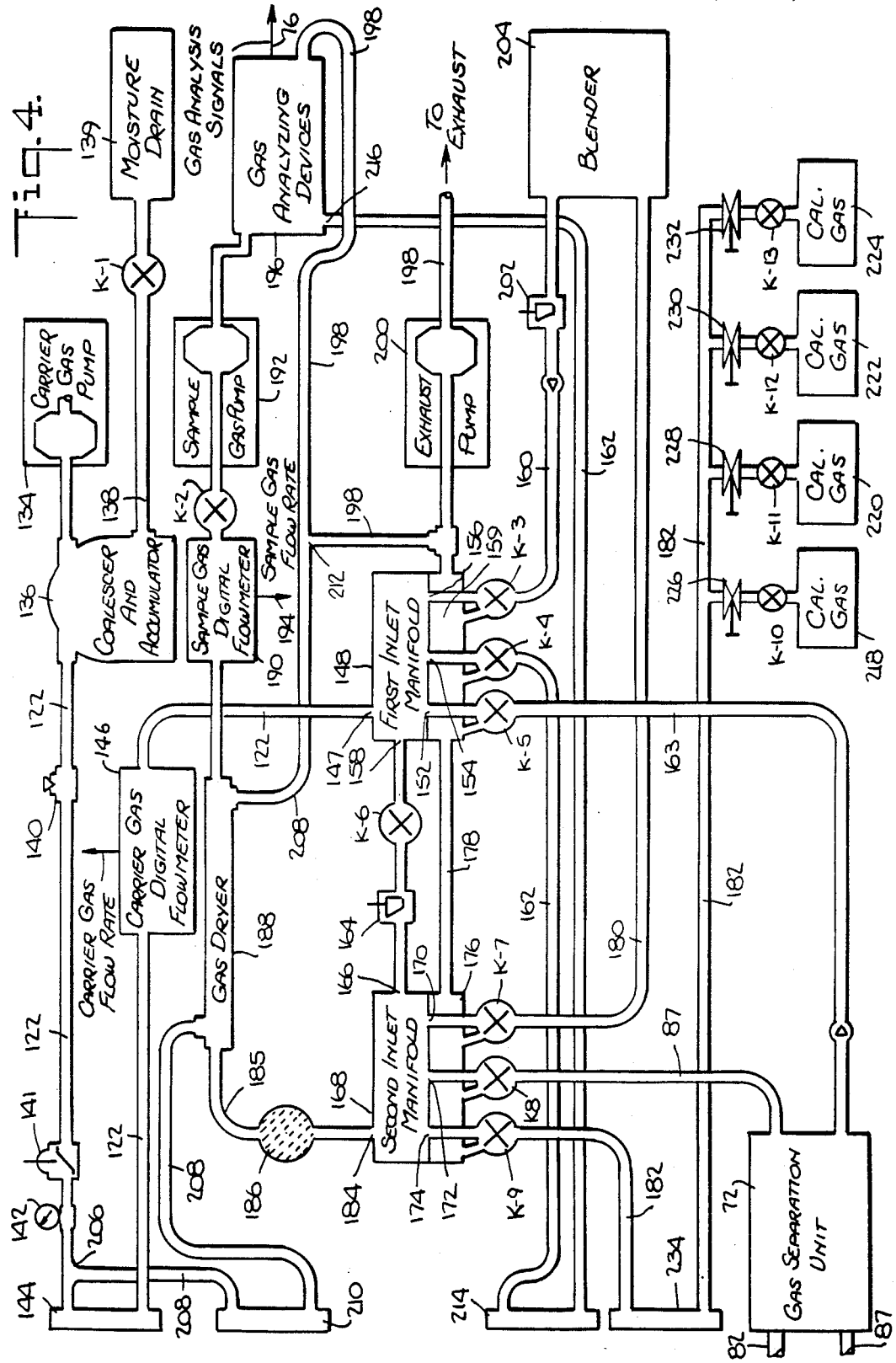
FIG. 4 is a diagrammatic representation of a gas flow control system for use in analyzing the gaseous components in the gas separated from the extracted mud.

The gas flow systems for supplying carrier gas to the gas separation unit 72 and for supplying sample gases to the gas collection and monitoring unit 74 are shown in FIG. 4.

In the arrangement of FIG. 4, air is chosen as the carrier gas because of its ready availability and because it is relatively inert with respect to the hydrocarbons contained in the mud gas. Other gases, such as nitrogen, may be used, for example where the ambient air contains an excess of impurities which could affect the sample gas measurements.

As shown in FIG. 4, there is provided a carrier gas pump 134 which pumps carrier gas through a coalescer and accumulator 136. The coalescer and accumulator operate to separate moisture from the pressurized carrier gas and to smooth out the impulses from the carrier gas pump 134. The separated moisture is directed via a moisture exhaust line 138 and a solenoid controlled on-off valve K-1 to a moisture drain 139. The pressurized carrier gas from the coalescer and accumulator 136 is supplied via the carrier gas line 122 through a pop-off pressure valve 140, a diaphragm regulator 141 and a pressure gauge 142 to a carrier gas rotometer 144. The pop-off pressure valve 140 is adjustable to open automatically when the pressure in the carrier gas line 122 exceeds a safe limit so as to exhaust carrier gas from the carrier gas line. The diaphragm regulator 141 is manually adjustable to a predetermined pressure and it operates to maintain that pressure downstream of the valve irrespective of pressure variations in the carrier gas line 122 upstream of the valve. The pressure gauge 142 indicates the pressure downstream of the regulator 141 for setting the regulator. The carrier gas rotometer 144 is a floating bead instrument which may be adjusted to control the flow rate of the carrier gas in the line 122. The diaphragm regulator 141, the pressure gauge 142 and the carrier gas rotometer 144 are well known components and their operation will not be described in detail herein.

The carrier gas in the line 122 passes from the rotometer 144 through a carrier gas digital flowmeter 146 to an inlet port 147 of a first inlet manifold 148. The digital flowmeter 146, which is a commercially available device, provides a digital electrical signal on a carrier gas flow signal line 150 which accurately represents the instantaneous rate of flow of the carrier gas in the line 122.

The first inlet manifold 148 is also provided with four outlet ports 152, 154, 156 and 158. Three of these ports, 156, 154 and 152 are connected, respectively, to a first individual port of associated solenoid controlled three-way valves K-3, K-4 and K-5. The three-way valves K-3, K-4 and K-5 each have a common port which is selectively connectable to either one of two individual ports. The individual port which is not connected to the common port is closed. The second individual port of each of the three-way valves K-3, K-4 and K-5 is connected to a first exhaust manifold 159 shown adjacent the first inlet manifold 148. The common ports of the three-way valves K-3, K-4 and K-5 are connected, respectively, to a blender supply line 160, a gas analyzer purge line 162 and a gas separation unit carrier gas supply line 163. The remaining outlet port 158 of the inlet manifold is connected to one port of a solenoid controlled on-off valve K-6. The other port of the valve K-6 is connected via a diaphragm type regulator valve 164 to one inlet port 166 of a second inlet manifold 168.

The second inlet manifold 168 has three additional inlet ports 170, 172 and 174 which are connected, respectively, to a first individual port of associated solenoid controlled three-way valves K-7, K-8 and K-9. The other individual port of these valves is connected to a second exhaust manifold 176. The first and second exhaust manifolds 158 and 176 are interconnected by an exhaust manifold connecting line 178. The common ports of the solenoid controlled three-way valves K-7, K-8 an K-9 are connected, respectively, to a blender return line 180, to the sample gas line 87 and to a calibration gas line 182.

The second inlet manifold 168 is provided with an outlet port 184 which is connected to a gas analyzer supply line 185. This line passes through a sample gas filter 186, a gas dryer 188, a sample gas digital flowmeter 190 and an on-off solenoid controlled valve K-2 to a sample gas pump 192. The sample gas filter 186 removes any solid matter which may have become entrained in the gas sample stream. The dryer 188 removes water vapor from the sample stream so as to reduce its interference with the gas analysis and in order to protect optical components. The sample gas digital flowmeter 190 is of the same construction as the carrier gas digital flowmeter 146 and it provides a digital signal on a sample gas flow signal line 194 which accurately represents the instantaneous rate of flow of the sample gas. The sample gas pump 192 is of the same construction as the carrier gas pump 134 and it serves to drive the sample gas through a group of gas analyzing devices indicated collectively at 196 in FIG. 4. These gas analyzing devices will be described in further detail hereinafter.

The gas analyzing devices 196 are provided with a gas exhaust line 198 which is connected to an exhaust pump 200 for discharging the analyzed gases to a safe exhaust location away from personnel and away from sources of flame.

The blender supply line 160 is connected via an adjustable diaphragm regulator 202 to a blender 204. The adjustable diaphragm regulator 202 is of the same construction as the regulators 141 and 164 and it serves to regulate the pressure of gases flowing to the blender 204. The blender is an auxiliary device that is used to separate gases which may be contained internally in the pores of the rock cuttings which are brought up from the bottom of the well with the mud. These rock cuttings are separated from the liquid portions of the mud in the shale shaker 54 (FIG. 1) and they are then finely ground in the blender 204 to release the gases entrapped in their pores. These released gases are mixed with carrier gas supplied via the blender supply line 160 to produce blender sample gas which is then returned along the blender return line 180 to the valve K-7 and from there through the second inlet manifold 168 and through the filter 186, the dryer 188, the second digital flowmeter 190, the valve K-2 and the sample gas pump 192 to the gas analyzers 196.

The dryer 188 operates to remove moisture from gases which are to be analyzed in the gas analyzers 196. While any drying device which can remove moisture from a flowing gas stream without appreciably affecting its pressure or flow rate can be used, it is preferred to use a hygroscopic ion exchange membrane type dryer wherein the gas stream to be dried flows along the inner surface of a polymer gelatin tube while a stream of drying gas flows along the outer surface of the tube. Water vapor from the gas stream to be dried migrates through the tube to the drying gas. An example of a suitable dryer of this type is sold under the name Perma Pure No. MD-250-12SS by Perma Pure Products Inc. of Toms River, N.J.

Drying air for the dryer 188 is diverted from the carrier gas line 122 at a "T" junction 206 located along the carrier gas line 122 between the pressure gauge 142 and the carrier gas rotometer 144. The drying gas flows from the "T" junction 206 through a dryer gas line 208 and through a dryer gas rotometer 210 to the dryer 188. After acquiring moisture in the dryer, the dryer gas continues to flow along the dryer gas line 208 to a junction 212; and from there it flows out through the exhaust gas line 198.

The gas analyzer purge line 162 extends from the valve K-4 to a purge gas rotometer 214 and from there back to a purge gas inlet 216 of the gas analyzers 196.

As shown in FIG. 4 there are provided a number of calibration gas supply tanks 218, 220, 222 and 224 which contain known concentrations of specific component gases in a carrier gas. These gases are selectively transferred via associated solenoid controlled on-off valves K-10, K-11, K-12 and K-13 and manual regulation valves 226, 228, 230 and 232 to the calibration gas line 182. A calibration gas rotometer 234 is interposed in the calibration gas line 182 to regulate the flow of these gases to the gas analyzers 196.

The various components used in the gas flow control system of FIG. 4 are individually well known and their specific configuration is not critical to the operation of the system. The following specific components are used in the presently preferred embodiment:

The carrier gas pump 134, the sample gas pump 192 and the exhaust gas pump 200 are all vibrating diaphragm type gas pumps which deliver 0.61 cubic feet (0.0173 cubic meters) per minute at zero gauge back pressure. Such pumps, like Gast Pump Part No. MDA-P101-AA, are available from Gast Manufacturing Corporation, Benton Harbor, Mich.

The coalescer/separator 136 is available from the Wright-Austin Company, Detroit, Mich.

The carrier gas, dryer gas, purge gas and calibration gas rotometers 144, 210, 214 and 234 are of a known type, such as that supplied by Dwyer Instruments Inc. of Michigan City, Ind. as Part No. RMA-26-SSV-PF. Although in FIG. 4 the gas flow is shown in a downward direction, the actual flow is upward through the rotometers. Each rotometer includes a needle valve for adjusting the flow; and the flow rate is indicated by the vertical position of a bead located in an upwardly divergent glass tube.

The sample gas filter 186 (which may actually be a series of filters) is an in-line dust filter such as supplied by Mine Safety Appliance Co. as filter Part No. 453831.

The carrier gas and sample gas digital flow meters 146 and 190 are of the type supplied by Flow Technology, Inc. of Phoenix, Ariz. and known as Series II Omniflow Turbine Flowmeters, Part No. FTD-N4, GJS. These flowmeters have turbine blades located in the path of gas flow that turn at a rate corresponding to the flow rate of the gas. The turbine blade shaft speed is measured by a magnetic pickup coil which produces pulses at a frequency corresponding to the shaft speed.

The gas flow control system of FIG. 4 provides the following modes of operation:

1. Analysis of sample gas from mud;
2. Analysis of sample gas from rock cuttings;
3. Zero setting of gas analyzing devices;
4. Calibration of gas analyzing devices;
5. Purge of gas analyzing devices; and
6. Backwash of gas separation unit.

The gas flows for these various modes of operation are controlled by the energization and deenergization of the solenoid controlled valves K-1 . . . K-13. In this connection, each of the open-close valves K-1, K-6 and K-10 through K-13 is normally closed in the deenergized condition and is open in the energized state while the open-close valve K-2 is normally open in the deenergized state and is closed in the energized state. The three-way valves K-3, K-4, K-7 and K-9 each interconnect their common or lower port to their respective inlet manifold port and close their exhaust manifold port in the energized state and interconnect their common or lower port to their respective exhaust manifold and close their inlet manifold port in the deenergized state. The three-way valves K-5 and K-8 each interconnect their common or lower port to their respective exhaust manifold port and close their inlet manifold port in the deenergized state and interconnect their common or lower port to their respective inlet manifold and close their exhaust manifold port in the energized state.

The various gas flows for each of the operational modes will now be discussed.

First Mode—Analysis of Sample Gas from Mud

In this mode the solenoid controlled valves K-5, K-6 and K-8 are energized while the other solenoid controlled valves are deenergized. Carrier gas flows from the carrier gas pump 134 along the carrier gas line 122 through the coalescer/accumulator 136, through the pop-off pressure valve 140, the diaphragm regulator 141, the pressure gauge 142, the carrier gas rotometer 144 and the carrier gas digital flowmeter 146 to the first inlet manifold 148. From there, the carrier gas flows through the solenoid controlled valve K-5 and through the gas separation unit supply line 163 to the gas separation unit 72 where it mixes the mud and mud gas flowing through that unit. In the course of this mixing, the carrier forms a mixture with the mud gas and the resulting sample gas mixture flows out from the gas separation unit 72 along the sample gas line 87 and through the solenoid controlled valve K-8 into the second inlet manifold 168. From there the sample gas flows along gas analyzer supply line 185 through the sample gas filter 186 and the dryer 188. The sample gas then flows through the digital flowmeter 190, the solenoid controlled valve K-2 and the sample gas pump 192 from which it is pumped through the sample gas analyzers 196 for analysis. After passing through the analyzers 196 the sample gas passes through the exhaust line 198 to the exhaust gas pump which pumps it to the safe exhaust.

During the movement of carrier and sample gas through the system, dryer gas is directed from the "T" junction 206 through the dryer gas rotometer 210 and through the dryer gas portion of the dryer 188 where it acquires moisture from the sample gas passing through the dryer. The moisturized dryer gas exits from the dryer and flows to the junction 212 in the exhaust gas line where it is diverted to exhaust.

The pressure and flow rates of the carrier and dryer gases are controlled by the diaphragm regulator 141 and the carrier gas and dryer gas rotometers 144 and 210. The precise rate of flow of the carrier gas, however, is measured by the carrier gas digital flowmeter 146. Digital electrical signals representative of this flow are transmitted via the carrier gas flow signal line 150 to the gas transducer interface unit 80 (FIG. 2). At the same time the precise rate of flow of the sample gas, i.e. the mixture of carrier gas and mud gas from the gas separation unit 72, is measured by the sample gas digital flow meter 190. Digital electrical signals representative of this flow are transmitted via the sample gas flow signal line 194 to the gas transducer interface unit 80 (FIG. 2).

The gas analyzing devices 196, which will be described more fully hereinafter, produce gas analysis signals which are transmitted via the gas analysis signal lines 76 to the gas transducer interface unit 80 (FIG. 2).

As can be seen in FIG. 2, the carrier and sample gas flow rate signals, as well as the gas analyzer signals, are transmitted from the gas interface unit 80 to the signal processor 64. Also, the sample mud flow rate signals are transmitted from the mud transducer interface unit 78 to the signal processor 64. The signals representing the mud sample flow rate, the carrier and sample gas flow rates and the gas analysis results are all processed in the signal processor 64 to give an output representative of (1) the stoichiometric amount of each of several gaseous constituents in the drilling mud, i.e. moles of gaseous component at standard atmospheric temperatures and pressure per liter of mud; and (2) the ratios of the various gaseous constitutents in the sample gas, i.e. moles of one gas component per mole of another gas component. In addition, signals representative of the drilling depth and the lag time for mud to flow from the drill bit at the bottom of the well up to the surface are processed in the signal processor 64 to provide a correlation between the gas concentration measurements and the well depth location which they represent. In this way there is provided an accurate log of the gas producing characteristics at each level down through the well.

Second Mode—Analysis of Sample Gas from Rock Cuttings

In this mode, the solenoid controlled valves K-3, K-5, K-7 and K-8 are energized while the other solenoid controlled valves are deenergized. As a result, carrier gas flows from the carrier gas pump 134 along the carrier gas line 122 to the first inlet manifold 148. From there the carrier gas flows through the solenoid controlled valve K-3 and through the blender supply line 160 and the diaphragm regulator valve 202 to the blender 204 where it mixes with gases which have been released by crushing rock cuttings brought up from the bottom of the well by the flowing mud. The resulting mixture of carrier gas and rock cutting gas leaves the blender 204 via the blender return line 180 and passes through the solenoid controlled valve K-7 to the second inlet manifold 168. From there the gas mixture passes along the gas analyzer supply line 185 through the sample gas filter 186, the dryer 188, the digital flow meter 190, the valve K-2 and the sample gas pump 192 to the gas analyzing devices 196. The gas is analyzed in the analyzing devices 196 and then passes through the exhaust line 198 to exhaust.

Third Mode—Zero Setting of Gas Analyzing Devices

In order to be certain that the gas analyzing devices 196 accurately indicate the concentration of gaseous components in the mud gas, they are first supplied with carrier gas free of any mud gas; and, while so supplied, the analyzing devices are adjusted to give a zero reading. In this mode, the solenoid controlled valves K-5, K-6 and K-8 are energized while the other solenoid controlled valves are deenergized. Carrier gas flows from the carrier gas pump 134 through the carrier gas line 122 to the first inlet manifold 148. From there the carrier gas exits via the outlet port 158 and passes through the solenoid controlled valve K-6 and the diaphragm regulator 164 to the input port 166 of the second manifold 168. The carrier gas then passes out through the outlet port 184 and along the gas analyzer supply line 185 through the filter 186, the dryer 188, the digital flow meter 190, the solenoid controlled valve K-2 and the sample gas pump 192 to the gas analyzing devices 196. Thus, pure carrier gas free of any mud gas is supplied to the gas analyzing devices 196 so that they may be adjusted accurately to a zero reading.

Fourth Mode—Calibration of Gas Analyzing Devices

In order to calibrate the gas analyzing devices, predetermined concentrations of each gaseous component to be detected are supplied to the analyzing devices. These predetermined concentrations are provided in the calibration gas supply tanks 218, 220, 222 and 224. It will be appreciated, of course, that the number of such tanks can vary according to the number of different gaseous components to be analyzed and according to the different concentrations to which the gas analyzing devices are to be calibrated. In this mode, the solenoid controlled valves K-5 and K-9 are energized together with one of the solenoid controlled valves K-10, K-11, K-12 or K-13 depending on which calibration gas is to be used. All other solenoid controlled valves are deenergized.

Calibration gas flows from the supply tank 218, 220, 222 or 224 whose solenoid controlled valve K-10, K-11, K-12 or K-13 is energized. This gas flows along the calibration gas line 182 and through the solenoid controlled valve K-9 into the second inlet manifold 168 and out through the outlet port 184. The calibration gas then flows along the gas analyzer supply line 185 through the sample gas filter 186, the dryer 188, the digital flow meter 190, the solenoid controlled valve K-2 and the sample gas pump 192 to the gas analyzing devices 196. The sample gas analyzing devices are then adjusted to give output signals which correspond to the known concentration of gaseous components in the calibration gas.

Also, during this mode of operation, the carrier gas flows through the first inlet manifold 148 and out through the solenoid controlled valve K-5 to the gas separation unit 72. The sample gas from the separation unit flows through the sample gas line 87 and through the deenergized solenoid controlled valve K-8 which diverts it to the second exhaust manifold 176. The sample gas then flows through the connecting line 178 to the first exhaust manifold 159 and from there through the exhaust line 198 and the exhaust gas pump 200 to exhaust. It will be appreciated that this arrangement permits continuous operation of the gas separation unit 72 during the calibration process, so that, when normal operation resumes, the sample stream sent to the analyzers will correspond to the sampled drilling fluid.

Fifth Mode—Purge of Gas Analyzing Devices

From time to time, and particularly before calibration and when switching between mud gas analysis and rock gas analysis, it is important to purge the gas analyzing devices 196 of gases from prior analyses. For this purpose, pure carrier gas is backwashed through the gas analyzing devices. In this mode of operation the solenoid controlled valves K-4 and K-5 are energized and the other solenoid controlled valves are deenergized. Carrier gas then flows from the carrier gas pump 134, through the carrier gas line 122 to the first inlet manifold 148. From there the carrier gas flows out through the solenoid controlled valve K-4, through the gas analyzer purge line 162 to the purge gas rotometer 214 where its flow rate is regulated. The carrier gas then continues along the gas analyzer purge line 162 to the purge gas inlet 216 of the gas analyzing devices 196. The carrier gas purges the gas analyzing devices of other gases from prior analyses by backwashing the analyzing devices. The gas exits the analyzing devices at the exhaust line 198 and passes through the exhaust pump 200 to exhaust.

Sixth Mode—Backwash of Gas Separation Unit

From time to time during operation of the system, the gas separation unit 72 becomes clogged in certain regions with mud; and as a result, particles of mud are carried along with the sample gas. These mud particles may adversely affect the carrier gas flow and they may have an adverse effect on the readings from the gas analyzing devices. Accordingly, when the amount of mud particles in the gas reaches a predetermined level, the gas separation unit 72 is backwashed with carrier gas. In this mode, the solenoid controlled valves K-8 and K-6 are energized and the other solenoid controlled valves are deenergized. Carrier gas flows from the carrier gas pump 134 through the carrier gas line 122 to the first inlet manifold 148. From there the carrier gas exits through the outlet port 158 and passes through the energized solenoid controlled valve K-6 and the regulator 164 to the inlet port 168 of the second inlet manifold 168. The carrier gas then flows through the solenoid controlled valve K-8 and through the sample gas line 87 and then passes in reverse direction through the gas separation unit 72. Upon exiting the gas separation unit, the carrier gas flows through the carrier gas line 163 to the deenergized solenoid controlled valve K-5 which diverts it to the first exhaust manifold 159. The gas then passes along the exhaust line 198 and through the exhaust gas pump 200 to exhaust.

It should be understood that the first mode, i.e. analysis of sample gas from mud, is carried out continuously with the drilling. That is, as drilling proceeds, the returned drilling mud is continuously passed through the gas separation unit 72 and the separated gas is continuously subjected to analysis in the gas analyzing devices 196. The other modes are carried out intermittently relative to the drilling operation. That is, they are carried out during the intervals when drilling does not take place, e.g. while a new length of drill string is being added or when the drill bit is being replaced.

Figure 5:
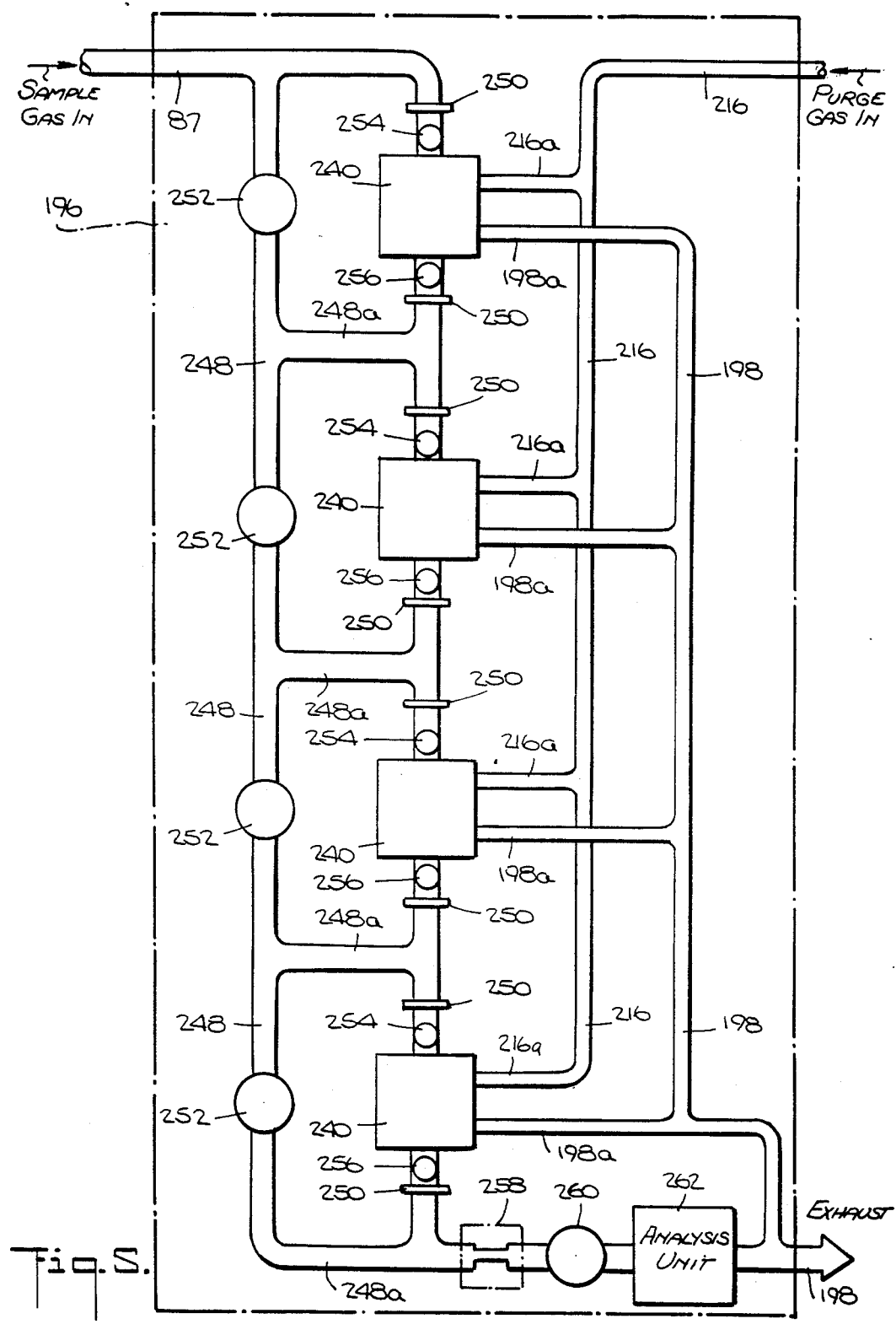
FIG. 5 is a diagrammatic representation of an arrangement of gas component analyzers used to measure the concentration of selected gaseous components in the gas separated from the extracted mud.

FIG. 5 shows in greater detail the gas analyzing devices 196. As shown, these devices comprise a plurality of infrared spectrophotometers 240, 242, 244 and 246 connected in series along the sample gas line 87. These spectrophotometers, which will be described in greater detail hereinafter, operate to produce electric signals which represent the concentration of a given gaseous component in the sample gas passing through them. Each spectrophotometer is set to monitor the concentration of a different gaseous component. A bypass line 248 is connected to extend in parallel with the spectrophotometers in the sample gas line 87; and branch lines 248a extend between the bypass line 248 and locations in the sample gas line 87 between adjacent spectrophotometers. The sample gas line 87 is provided with automatic gas closure fittings 250 on each side of each spectrophotometer. These fittings open when the spectrophotometer is in place as shown in FIG. 5 but they close automatically when the spectrophotometer is removed. When this happens, the sample gas in the line 87 passes to the bypass line 248 and then back through the next succeeding branch line 248a to the next succeeding spectrophotometer. In order to direct the bypassed gas around only that location where a spectrophotometer had been removed, bypass valves 252 are provided in the bypass line 248 between each of the several branch lines 248a. These valves are normally closed but each valve is arranged to be opened when its corresponding spectrophotometer is removed.

A pressure sensor 254 and a temperature sensor 256 are located in the sample gas line 87 at each spectrophotometer bench. These sensors produce electrical signals representative of the pressure and temperature of the sample gas passing through the spectrophotometers. These pressure and temperature signals are transmitted to the transducer interface unit 92 (FIG. 2) and to the signal processor 64 to be processed with output signals from the spectrophotometers 240, 242, 244 and 246 to convert the gas concentrations actually measured to corresponding concentrations at standard conditions of temperature and pressure.

As shown the purge line 216 extends along the spectrophotometers and is provided with branch lines 216a leading into each spectrophotometer to supply purge gas in the fifth mode of operation described above. The purge gas leaves each spectrophotometer by means of branch lines 198a of the gas exhaust line 198.

A pressure regulator 258 is interposed in the sample gas line 87 downstream of the spectrophotometers. This pressure regulator maintains an equivalent level of backpressure in the spectrophotometers so that when the respective concentration values are corrected to standard temperature and pressure conditions, relative errors will be minimized; thereby reducing the errors in calculating concentration ratios.

The flow out of the pressure regulator 258 passes through a safety shutoff valve 260 and through a further analysis unit 262 which measures the thermal conductivity, combustability, the hydrogen concentration and the hydrogen sulfide concentration of the sample stream. These measurements are well known and do not per se form part of the invention. Accordingly, the details of the analysis unit 262 will not be described herein. The outputs of the analysis unit 262 and the purge line 216 are connected to the exhaust line 198.

Figure 6:
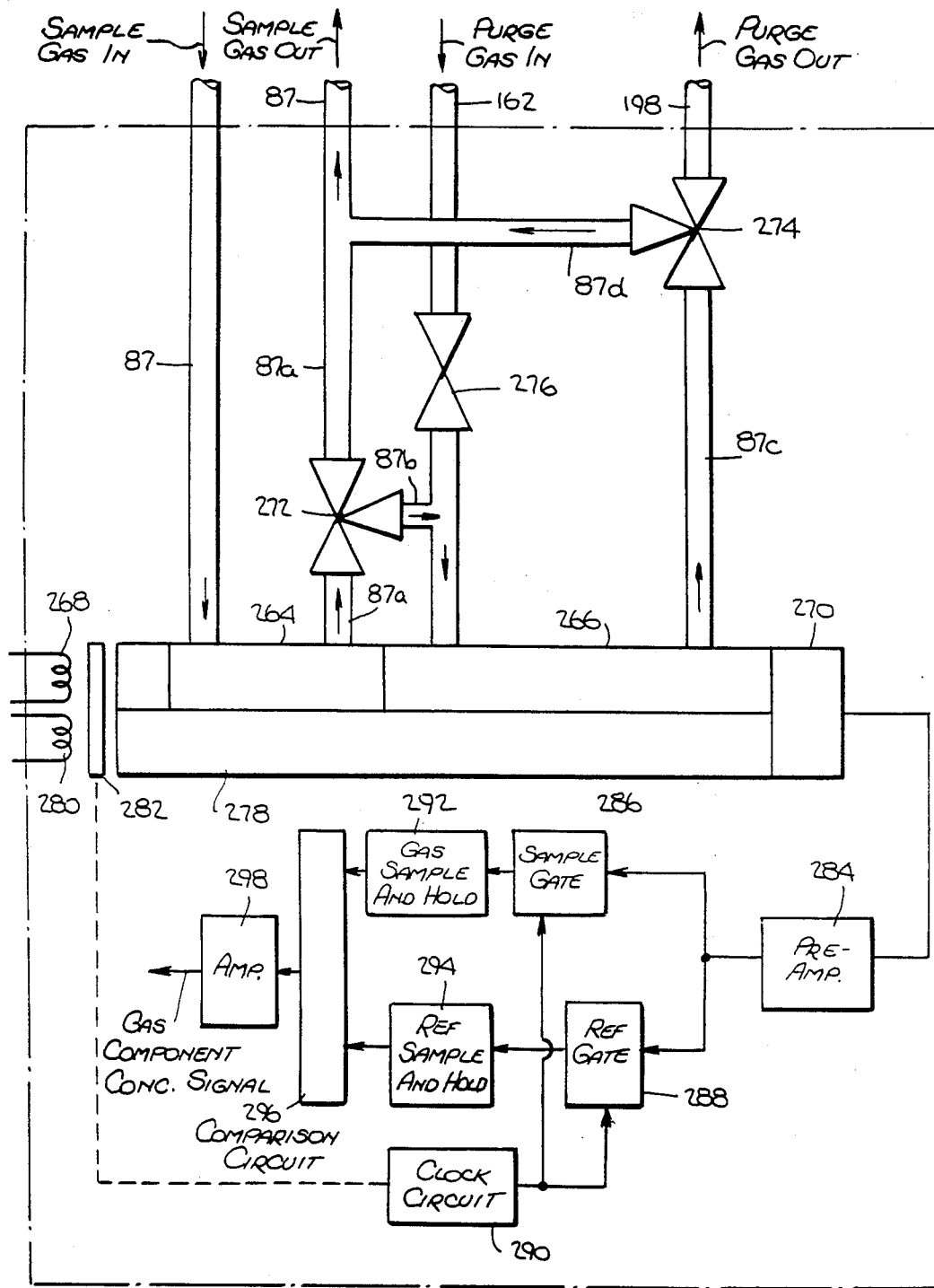
FIG. 6 is a schematic showing the general construction and operation of a gas component analyzer shown in FIG. 5.

FIG. 6 shows schematically a typical one of the infrared spectrophotometers 240, 242, 244 and 246 and the gas flow line arrangements used in connection therewith. These infrared spectrophotometers per se are well known. An example of a typical spectrophotometer is the shown in the U.S. Pat. Re. No. 31,438. The spectrophotometer construction shown in FIG. 6 provides an expanded range of sensitivity by arranging two cells, i.e. a high concentration cell 264 and a low concentration cell 266, in series between an infrared lamp 268 and an infrared detector 270. Sample gas flowing along the sample gas line 87 passes into one end of the high concentration cell 264 and out through a first output line 87a at the other end of the cell. If the concentration of a particular gaseous component to be sensed in the sample gas is very low, the infrared beam will not be attenuated very much by the sample gas flowing through the high concentration cell 264. In such case the sample gas flowing through the output line 87a is directed through a first three-way valve 272 and a first crossover line 87b and back into one end of the low concentration cell 266. The sample gas thus passes through both cells 264 and 266 in series and produces a greater attenuation of the infrared beam passing through the cells. The sample gas exits from the far end of the low concentration cell 266 via a second output line 87c through a second three-way valve 274 and a second crossover line 87d back to the sample gas line 87 where it is directed to the next infrared spectrophotometer. When the gaseous component being measured is of a high concentration so that it produces substantial attenuation of the infrared beam in the high concentration cell 264, the gas exiting via the first output line 87a is directed by the first three-way valve 272 back into the sample gas line 87. In such case, purge gas is directed from the purge line 162 through an open-close valve 276 into the low concentration cell 266 and back out through the second output line 87c and the second two-way valve 274 back to the purge exhaust line 198.

As can be seen in FIG. 6 there is provided a sealed reference cell 278 in parallel with the high and low concentration cells 264 and 266. A separate infrared lamp 280 is provided to direct an infrared beam through the reference cell 278. However, the reference cell 278 and the high and low concentration cells 264 and 266 share the same infrared detector 270. A shutter 282 is arranged in front of the lamps 268 and 280 and is rotated by suitable means (not shown) so that at any instant either one or the other infrared beam, but not both, is directed at the detector 274. The detector output is amplified in a preamplifier 284 and is applied to sample and reference gates 286 and 288. The gates in turn are controlled by a clock circuit 290 which also controls the shutter 282. Thus, whenever the shutter allows the beam from the infrared lamp 268 to pass through the high and low concentration cells 264 and 266, the sample gate 286 is open and signals produced by the detector 270 are directed through that gate to a sample gas sample and hold circuit 292. On the other hand, whenever the shutter 282 allows the beam from the infrared lamp 280 to pass through the reference cell 278, the reference gate 288 is open and signals produced by the detector 270 are directed through that gate to a reference sample and hold circuit 294. The outputs from the sample and hold circuits 292 and 294 are compared in a ratio type comparison circuit 296 and its output is amplified in a logarithmic amplifier 298. The output from the logarithmic amplifier 298 is directed to the gas transducer interface unit 80 (FIG. 2) and from there to the signal processor 64 for further processing.

Each of the infrared spectrophotometers 240, 242, 244 and 246 (FIG. 6) is sensitive to the presence of a different constituent of the sample gas which passes through it. This selective sensitivity is obtained by the tuning of the infrared detector 270 (FIG. 6). Thus, for example, where the concentration of methane (CH$_4$) is to be ascertained, the detector 270 is tuned by using absorptive filters to sense the attenuation of infrared frequencies or wavelengths which are absorbed by methane, i.e. 7.7 microns. Other gaseous constituents are sensed by tuning the detectors in the other spectrophotometers accordingly. For example, one spectrophotometer may also be tuned to sense wavelengths of about 12 microns to measure the concentration of ethane; another may be tuned to sense wavelengths of about 9.5 microns to measure the concentration of propane; and others, respectively, may be tuned to sense wavelengths of 8.5, 10.4 and 7.9 microns to measure the concentration of isobutane, butane and neopentane.

The signals from the spectrophotometers 240, 242, 244 and 246 (FIG. 5) as well as the signals from the carrier gas digital flow meter 146 and the sample gas digital flow meter 190 (FIG. 4) and signals from the mud flow rate detector 100 (FIG. 3) are supplied to the signal processor 64 and are combined to provide outputs which represent, on a continuous basis, the instantaneous ratio of each of the the measured hydrocarbon constituents to methane in the mud gas, as well as the concentration of each measured hydrocarbon constituent in the mud being returned from the well. In addition, data representing the depth of the well is supplied to the signal processor 64 on a continuous basis from suitable conventional well depth measuring means and additional data is generated in suitable fashion which represents the transit time for mud to pass from the bottom of the well to the mud sample pump 68 and the gas separation unit 72. This data represents the depth from which the calculated mud gas constituent ratios and concentrations were originated. As a result, there is obtained a continuous log of the gas bearing characteristics of the earth along the entire length of the well.

The signal processor processes the various signals representing sample and carrier gas flow rates, mud flow rate, gaseous component concentrations, well depth, and mud flow lag time by means of appropriate software which will, of course, be selected according to the particular hardware employed. In any event, to achieve a continuous log of the ratio of methane to other hydrocarbon gases, the signals from the infrared spectrophotometer which detects methane are separately compared in ratio type comparisons with the signals from the other infrared spectrophotometers. Also, to achieve a continuous log of the concentration of any given hydrocarbon constituent in the returned mud in cases where essentially all of the gas in the returned mud is separated from the mud in the gas separation unit 72, the value of the signal representative of sample gas flow rate is divided, on a continuous basis, by the value of the signal representative of mud flow rate; and is multiplied on a continuous basis, by the value of the signal from the infrared spectrophotometer tuned to sense that given hydrocarbon constituent. In cases where less than all of the gas in the returned mud is separated in the gas separation unit 72, an accurate representation of the concentration of a given gaseous constituent in the mud is obtained by dividing, on a continuous basis, the value of the signal representative of the carrier gas flow rate by the value of the signal representative of mud flow rate and multiplying same, on a continuous basis, by the value of the signal from the infrared spectrophotometer tuned to sense the concentration of that given hydrocarbon content.

I claim:

1. In the logging of a well during drilling thereof, the method of producing a logging signal which represents, on a continuous basis, the instantaneous concentration of a given gaseous component in drilling mud as it is being returned from the well, said method comprising the steps of:

continuously subjecting at least a portion of said drilling mud being returned from the well to gas separation to separate gas containing said gaseous component from said portion of the returned mud;

continuously and simultaneously subjecting the separated gas to analysis to produce a gaseous component concentration signal whose value at any instant corresponds to the concentration, at that instant, of said given gaseous component in the separated gas;

producing a continuous mud flow rate signal whose value at each instant corresponds to the rate of flow of drilling mud from which the gas is separated;

producing a continuous gas flow rate signal whose value at each instant corresponds to the rate of flow of gas separated from said drilling mud; and continuously processing said gaseous component concentration signal, said mud flow rate signal and said gas flow rate signal to provide a continuous logging signal whose value at any instant corresponds to the product of the concentration at that instant of the given gaseous component and the rate of flow at that instant of gas separated from said drilling mud divided by the rate of flow at that instant of the drilling mud.

2. A method according to claim 1 wherein the mud being returned from the well is directed into a header tank and a portion of the mud entering the header tank is pumped through a gas separation unit to separate gas from the mud passing through the gas separation unit.

3. A method according to claim 1 wherein the mud pumped through the gas separation unit is also pumped through a mud analysis unit and is subjected to analysis of its liquid components.

4. A method according to claim 1 wherein a further signal is produced which represents, on a continuous basis, the depth of the well from which the gas containing said different gaseous components was extracted and wherein said further signal is correlated, on a continuous basis, with said logging signal to produce a continuous representation of the logging signal correlated with the depth of the well.

5. A method according to claim 1 wherein different analyses are carried out to produce different logging signals by passing the gas containing said gaseous components through plural spectrophotometers each tuned to a different wavelength corresponding to the spectral absorption characteristic of said different gaseous components.

6. A method according to claim 5 wherein the gas containing said gaseous components is passed through said spectrophotometers in succession.

7. A method according to claim 1 wherein the drilling mud is subjected to gas separation by causing a carrier gas to mix with the mud and the gas contained in the mud.

8. A method according to claim 1 wherein the step of producing a continuous mud flow rate signal is carried out by pumping a selected portion of the drilling mud being returned from the well to a gas separation device and by measuring the rate at which said selected portion is pumped.

9. A method according to claim 1 wherein the step of producing a continuous gas flow rate signal comprises measuring the rate of flow of gas following its separation from the mud and prior to subjecting said gas to analysis.

10. Apparatus for producing a logging signal which represents, on a continuous basis, the instantaneous concentration of a given gaseous component in drilling mud as it is being returned from a well during the drilling thereof, said apparatus comprising:

means for continuously subjecting at least a portion of drilling mud being returned from a well being drilled to gas separation to separate gas containing said gaseous component from said portion of the returned mud;

means for continuously and simultaneously subjecting the separated gas to analysis to produce a gaseous component concentration signal whose value at each instant corresponds to the concentration, at that instant, of said give gaseous component in the separated gas;

means producing a continuous mud flow signal whose value at each instant corresponds to the rate of flow of drilling mud from which the gas is separated;

means for producing a continuous gas flow rate signal whose value at each instant corresponds to the rate of flow of gas separated from said drilling mud; and means for continuously processing said gaseous component concentration signal, said mud flow rate signal and said gas flow rate signal to provide a continuous logging signal whose value at each instant corresponds to the product of the concentration at that instant of the given gaseous component and the rate of flow at that instant of gas separated from said drilling mud divided by the rate of flow at that instant of the drilling mud.

11. Apparatus according to claim 10 wherein said means for continuously subjecting at least a portion of the drilling mud being returned from a well being drilled to gas separation comprises a header tank into which said mud is directed, a gas separation device and a mud pump connected to pump mud through said gas separation device, said mud pump and gas separation device together having a mud intake and a mud outlet in communication with the mud in said header tank, the mud intake being positioned near the mud inlet of said header tank.

12. Apparatus according to claim 11 wherein a mud analysis unit is connected in line with said mud pump and said gas separation device, said mud analysis unit being constructed to analyze the liquid components of the mud passing therethrough.

13. Apparatus according to claim 10 wherein said apparatus includes a well depth measuring means arranged to produce well depth signals which represent, on a continuous basis the depth of the well being drilled and a signal processing device for correlating on a continuous basis said logging signal and the well depth signals to produce a continuous representation of the logging signal correlated with the depth of the well.

14. Apparatus according to claim 10 wherein said means for subjecting the separated gas to analysis includes a plurality of spectrophotometers each tuned to a different wavelength corresponding to the spectral absorption characteristic of said different gaseous components.

15. Apparatus according to claim 14 wherein said means for subjecting the separated gas to analyses further includes means for directing the gas containing said gaseous components through said spectrophotometers in succession.

16. Apparatus according to claim 15 wherein at least some of said spectrophotometers comprise plural cells arranged in line with each other between an infrared lamp and an infrared detector and means for alternately directing gas through one or more cells to provide different measurement ranges.

17. Apparatus according to claim 10 wherein said means for subjecting mud to gas separation comprises an agitation type device and means arranged to cause a carrier gas to become intermixed with the mud flowing through said agitation type device.

18. Apparatus according to claim 10 wherein said means for continuously processing said gaseous component concentration signal, said mud flow rate signal and said gas flow rate signal comprises a signal processing means for producing signals corresponding to the product of the values of said gaseous component concentration signal and said gas flow rate signal divided by the value of said mud flow rate signal.

19. Apparatus according to claim 10 wherein the means producing a continuous mud flow signal comprises a sensor connected to monitor the speed at which said mud pump is driven.

20. Apparatus according to claim 10 wherein the means producing a continuous gas flow rate signal comprises a gas flow rate sensor connected in a gas flow line interconnecting said gas separation device and said means for subjecting the separated gas to analysis.

21. Apparatus according to claim 20 wherein said gas flow rate sensor is a digital flowmeter.

22. A method of ascertaining the concentration of at least one component of the mud gas in drilling mud during a well drilling operation, said method comprising the steps of:

continuously passing said drilling mud through an agitating type gas separation device;

simultaneously flowing a carrier gas through the mud gas separation device at a rate such that the volume of carrier gas is at least several times greater than the volume of mud gas in the drilling mud;

thoroughly mixing the carrier gas in said mud gas separation device with all of the mud therein as well as with the mud gas contained in the mud;

separating from said mud gas separation device a gas mixture comprising said carrier gas and said mud gas;

subjecting said gas mixture to measurement to produce a component gas signal whose value corresponds to the concentration of said component in said gas mixture;

measuring the volume of said carrier gas which flows into said mud gas separation device to produce a carrier gas signal whose value corresponds to said volume of said carrier gas;

measuring the quantity of the mud which passes through said mud gas separation device to produce a mud quantity signal whose value corresponds to said quantity of mud; and combining said component gas, carrier gas and mud quantity signals such that the product of the values of the component gas and carries gas signals is divided by the value of the mud quantity signal to produce a concentration signal whose value substantially corresponds to the concentration of said component gas in said drilling mud.

23. A method according to claim 22 wherein the mud is returned from the well and is directed into a header tank and a portion of the mud entering the header tank is pumped through a gas separation unit to separate gas from the mud passing through the gas separation unit.

24. A method according to claim 23 wherein the mud pumped through the gas separation unit is also pumped through a mud analysis unit and is subjected to analysis of its liquid components.

25. A method according to claim 22 wherein a further signal is produced which represent, on a continuous basis, the depth of the well from which the gas containing said different gaseous components was extracted and wherein said further signal is correlated, on a continuous basis, with said concentration signal to produce a continuous representation of the concentration signal correlated with the depth of the well.

26. A method according to claim 22 wherein different analyses are carried out by passing the gas containing said gaseous components through plural spectrophotometers each tuned to a different wavelength corresponding to the spectral absorption characteristic of said different gaseous components.

27. A method according to claim 26 wherein the gas containing said gaseous components passed through said spectrophotometers in succession.

28. A method according to claim 22 wherein the step of measuring the quantity of mud which passes through said mud gas separation device is carried out by continuously pumping mud through said mud gas separation device and measuring the speed of said pumping.

29. A method according to claim 22 wherein the step of measuring the volume of carrier gas which flows into said mud gas separation device comprises a gas flow rate sensor connected in a gas flow line through which carrier gas flows to said mud gas separation device.

30. A method according to claim 29 wherein said gas flow rate sensor is measured digitally.

31. Apparatus for producing a signal representative of the concentration of at least one component of the mud gas in drilling mud during a well drilling operation, said apparatus comprising:

an agitating type mud gas separation device;

means for passing drilling mud, from a well being drilled, through the mud gas separation device;

means for simultaneously flowing a carrier gas through the mud gas separation device at a rate such that the volume of carrier gas is at least several times greater than the volume of mud gas in the drilling mud, said agitating type mud gas separation device being operative to thoroughly mix the carrier gas with all of the mud therein as well as with the mud gas contained in the mud;

means for separating from said mud gas separation device a gas mixture comprising said carrier gas and said mud gas;

means for measuring the concentration of at least one component of the mud gas in the mixture and producing a component gas signal whose value corresponds to the concentration of said component in said mixture;

means for measuring the volume of said carrier gas which flows into said mud gas separation device and producing a carrier gas signal whose value corresponds to said volume of said gas;

means for measuring the quantity of the mud which passes through said mud gas separation device and producing a mud quantity signal whose value corresponds to said quantity of mud; and means for combining said component gas, carrier gas, and mud quantity signals such that the product of the values of the component gas and carrier gas signals is divided by the value of the mud quantity signals and for producing a concentration signal whose value substantially corresponds to the concentration of said component in said drilling mud.

32. Apparatus according to claim 31 wherein said gas separation device is connected in series with a mud pump and having a mud inlet and a mud outlet arranged in communication with the mud in a header tank and further arranged with the mud inlet located adjacent a mud intake of said header tank at which mud flows into said header tank the well being drilled.

33. Apparatus according to claim 32 wherein a mud analysis unit is connected in line with said mud pump and said gas separation device, said mud analysis unit being constructed to analyze the liquid components of the mud passing therethrough.

34. Apparatus according to claim 31 wherein said apparatus includes a well depth measuring means arranged to produce well depth signals which represent, on a continuous basis the depth of the well being drilled and a signal processing device for correlating on a continuous basis said concentration signal and the well depth signals to produce a continuous representation of the concentration of said given component correlated with the depth of the well.

35. Apparatus according to claim 34 wherein said means for measuring the concentration of at least one component of the mud gas in the mixture comprises a plurality of spectrophotometers each tuned to a different wavelength corresponding to the spectral absorption characteristic of said different gaseous components.

36. Apparatus according to claim 35 wherein said means or measuring the concentration of at least one component of the mud gas in the mixture includes means for directing the gas containing said gaseous components through said spectrophotometers in succession.

37. Apparatus according to claim 36 wherein at least some of said spectrophotometers comprise plural cells arranged in line with each other between an infrared lamp and an infrared detector and means for alternately directing gas through one or more cells provide different measurement ranges.

38. Apparatus according to claim 31 wherein the means for combining said component gas, carriers gas and mud quantity signals comprises a signal processor constructed and arranged to multiply the values of the component gas and carrier gas signals and to divide said product by the value of the mud quantity signal.

39. A mud gas test system for testing the gases contained in drilling mud returned from a well being drilled, said system comprising: a gas analyzing device for analyzing gases separated from the drilling mud, a mud gas separation device having a mud inlet, a mud outlet, a carrier gas inlet and a gas mixture outlet, said mud gas separation device being of the type in which carrier gas is mixed with mud passing therethrough to produce a gas mixture with gas contained in the mud, first and second manifolds, means arranged to supply a carrier gas to said first manifold, means, including a first valve, connecting the carrier gas inlet of said mud gas separation device to said first manifold, means, including a second valve, connecting the gas mixture outlet of said mud gas separation device to said second manifold, means including a third valve interconnecting said first and second manifolds and means interconnecting said second manifold and said gas analyzing device.

40. A mud gas test system according to claim 39 wherein said means interconnecting said second manifold and said gas analyzing device includes a fourth valve and wherein at least said first valve is of a switching type for alternately connecting the carrier gas inlet of said mud gas separation device to said first manifold and to exhaust.

41. A mud gas test system according to claim 40 wherein said second valve is of a switching type for alternately connecting the gas mixture outlet of said mud gas separation device to said second manifold and to exhaust.

42. A mud gas test system according to claim 41 wherein a rock gas separation device is connected via fifth and sixth valves, respectively, between said first and second manifolds.

43. A mud gas test system according to claim 42 wherein fifth valve is of a switching type for alternately connecting said rock gas separation device to said first manifold and to exhaust.

44. A mud gas test system according to claim 42 wherein said sixth valve is of a switching type for alternately connecting said rock gas separation device to said second manifold and to exhaust.

45. A mud gas test system according to claim 39 wherein a source of calibration gas is connected via a calibration gas valve to said second manifold.

46. A mud gas test system according to claim 39 wherein said first manifold is connected via a purge gas valve to a purge gas inlet of said gas analyzing device.

47. A method for determining whether hydrocarbons are present in earth formations as a borehole is drilled therethrough by earth-boring apparatus operatively supported by a string of drill pipe in said borehole for progressively excavating said borehole as a drilling mud is circulated downwardly through said drill string and returned to the surface through said borehole and including the steps of:
continuously intermixing an inert gas with at least a portion of said drilling mud returning to the surface while said earth-boring apparatus is progressively excavating said borehole for obtaining a mixed stream of said inert gas and at least a measurable portion of formation hydrocarbons that are entrained in successive portions of said returning drilling mud;
analyzing said mixed stream of gases for obtaining a first measurement representative of the concentration of at least one formation hydrocarbon in successive portions of said mixed stream;
analyzing said inert gas for obtaining a second measurement representative of the concentration of at least said one formation hydrocarbon in said inert gas;
correllating said first and second measurements for providing an output signal representative of the concentration of said formation hydrocarbon entrained in said returning drilling mud; and
plotting said output signals as a function of borehole depth for determining which of said subsurface formations may contain said formation hydrocarbon.

48. The method of claim 47 further including the step of analyzing a hydrocarbon having a known concentration for providing a calibration measurement to correct said first measurement.

49. The method of claim 47 wherein said first measurement is a series of continuous measurements obtained while said borehole is being excavated and said second measurement is a single measurement obtained while one or more additional joints of drill pipe are being coupled to said drill string.

50. The method of claim 49 further including the step of analyzing a hydrocarbon having a known concentration for providing a calibration measurement to correct said first measurement.

51. The method of claim 47 wherein said first measurement is a series of continuous measurements obtained while said borehole is being excavated and said second measurement is a series of periodic measurements successively obtained while additional joints of drill pipe are being successively coupled to said drill string.

52. A method for determining whether hydrocarbons are present in earth formations as a borehole is drilled therethrough by earth-boring apparatus operatively supported by a string of drill pipe in said borehole for progressively excavating said borehole as a drilling mud is circulated downwardly through said drill string and returned to the surface through said borehole and including carrying formation cuttings and entrained formation fluids and including the steps of:

continuously intermixing an inert gas with at least a portion of said drilling mud returning to the surface while said earth-boring apparatus is progressively excavating said borehole for obtaining a first mixed stream of said inert gas and at least a measurable portion of formation fluids that are entrained in successive portions of said returning drilling mud;

analyzing said first mixed streams of gases for obtaining a first measurement representative of the concentration of at least one formation fluid in successive portions of said first mixed stream;

intermixing said inert gas with at least a portion of said cuttings returning to the surface for obtaining a second mixed stream of said inert gas and at least a measurable portion of formation fluids that may be entrained in successive portions of said formation cuttings;

analyzing said second mixed stream of gases for obtaining a second measurement representative of the concentration of at least one formation fluid entrained in successive portions of said formation cuttings;

analyzing said inert gas for obtaining a third measurement representative of the concentration of at least said formation fluid in said inert gas;

correllating said measurements for providing a series of output signals representative of the concentration of said formation fluid entrained in said returning drilling mud and said cuttings; and plotting said output signals as a function of borehole depth for determining which of said subsurface formations may contain said formation fluid.

53. The method of claim 52 further including the step of analyzing a hydrocarbon having a known concentration for providing a calibration measurement to correct said first measurement.

54. The method of claim 52 wherein said first and second measurements are a series of continuous measurements obtained while said borehole is being excavated and said third measurement is a single measurement obtained while one or more additional joints of drill pipe are being coupled to said drill string.

55. The method of claim 54 further including the step of analyzing a hydrocarbon having a known concentration for providing a calibration measurement to correct said first and second measurements.

56. The method of claim 52 wherein said first and second measurement is a series of continuous measurements obtained while said borehole is being excavated and said third measurement is a series of periodic measurements successively obtained while additional joints of drill pipe are being successively coupled to said drill string.

* * * * *